United States Patent
Kume et al.

(10) Patent No.: US 9,563,965 B2
(45) Date of Patent: Feb. 7, 2017

(54) PROCESSING DEVICE FOR ULTRASONIC TOMOGRAPHIC IMAGE

(75) Inventors: Shinji Kume, Hiroshima (JP); Seiji Hama, Hiroshima (JP); Masaru Murashita, Mitaka (JP); Takashi Okada, Mitaka (JP)

(73) Assignee: HITACHI, LTD., Tokyo (JP)

( * ) Notice: Subject to any disclaimer, the term of this patent is extended or adjusted under 35 U.S.C. 154(b) by 776 days.

(21) Appl. No.: 12/911,865

(22) Filed: Oct. 26, 2010

(65) Prior Publication Data
US 2011/0105902 A1 May 5, 2011

(30) Foreign Application Priority Data
Nov. 5, 2009 (JP) ................. 2009-253665

(51) Int. Cl.
*A61B 8/00* (2006.01)
*G06T 7/20* (2006.01)
*A61B 8/08* (2006.01)
*A61B 8/14* (2006.01)

(52) U.S. Cl.
CPC ........... *G06T 7/2006* (2013.01); *A61B 8/0891* (2013.01); *A61B 8/14* (2013.01); *A61B 8/5253* (2013.01); *G06T 2207/10072* (2013.01); *G06T 2207/10136* (2013.01); *G06T 2207/20148* (2013.01); *G06T 2207/20224* (2013.01); *G06T 2207/30048* (2013.01); *G06T 2207/30101* (2013.01)

(58) Field of Classification Search
CPC ......... A61B 5/055; A61B 8/543; A61B 5/742; A61B 5/0073; A61B 5/024; A61B 5/7253; A61B 5/0095; A61B 5/7257
USPC .......................................... 600/443
See application file for complete search history.

(56) References Cited

U.S. PATENT DOCUMENTS

2005/0249391 A1 * 11/2005 Kimmel et al. .............. 382/128
2006/0171585 A1    8/2006 Rinck et al.
2008/0242977 A1   10/2008 Sirohey et al.
(Continued)

FOREIGN PATENT DOCUMENTS

CN    101081171 A    12/2007
CN    101175442 A     5/2008
(Continued)

OTHER PUBLICATIONS

Extended European Search Report dated Sep. 7, 202, issued in corresponding European Patent Application No. 10013970.8 (8 pages), Incomplete Date, Sep. 7, 2012.
(Continued)

*Primary Examiner* — Joel Lamprecht
(74) *Attorney, Agent, or Firm* — Westerman, Hattori, Daniels & Adrian, LLP

(57) ABSTRACT

A free-moving piece (jellyfish sign) having a high probability of separation in the near future in an unstable plaque is clearly displayed. Ultrasonic tomographic images (25) of a cross section including an axis of the carotid artery are successively obtained. Using a threshold value which sets a surface (48) of the unstable plaque as a boundary between brightness and darkness, the plurality of ultrasonic tomographic images (25) are binarized. A difference is calculated between corresponding pixels of two binarized ultrasonic tomographic images so that a free-moving piece (52) is extracted and displayed overlapped over the ultrasonic tomographic image (25).

10 Claims, 8 Drawing Sheets

(56) References Cited

U.S. PATENT DOCUMENTS

| | | | |
|---|---|---|---|
| 2008/0281205 A1* | 11/2008 | Naghavi et al. | 600/458 |
| 2009/0069680 A1 | 3/2009 | Abe | |
| 2009/0214090 A1* | 8/2009 | Hayes | 382/128 |
| 2010/0049049 A1* | 2/2010 | Asao et al. | 600/443 |

FOREIGN PATENT DOCUMENTS

| | | |
|---|---|---|
| CN | 101347341 A | 1/2009 |
| CN | 101361665 A | 2/2009 |
| CN | 101518440 A | 9/2009 |
| EP | 2226013 A1 | 9/2010 |
| JP | 62-189054 A | 8/1987 |
| JP | 2008-073282 A | 4/2008 |
| JP | 2009-022414 A | 2/2009 |
| JP | 2009-148395 A | 7/2009 |

OTHER PUBLICATIONS

Vavuranakis, M. et al., "A new method for assessment of plaque vulnerability based on vasa vasorum imaging, by using contrast-enhanced intravascular ultrasound and differential image analysis", International Journal of Cardiology, Elsevier Science Publishers, Amsterdam, NL, vol. 130, No. 1, Oct. 30, 2008, pp. 23-29, XP025950568.

Demaria, A. N. et al. "Imaging Vulnerable Plaque by Ultrasound", Journal of the American College of Cardiology, Elsevier, New York, NY, US, vol. 47, No. 8, Apr. 18, 2006, pp. C32-C39, XP028006135.

Chinese Office Action dated Nov. 5, 2013, issued in Chinese Patent Application No. 201010536594.X, w/ English translation (10 pages).

* cited by examiner

PROCESSING DEVICE FOR ULTRASONIC TOMOGRAPHIC IMAGE

BACKGROUND

Technical Field

The present invention relates to ultrasonic diagnosis in which ultrasound is transmitted to and from a subject and an ultrasonic tomographic image is obtained, and in particular, to an image process of a tomographic image of a blood vessel.

Background Art

Properties of plaques attached to an inner surface of a blood vessel wall observed in arteriosclerosis or the like may be classified primarily into four types, including fibrous, calcified, fatty, and bleeding. The fibrous and calcified plaques are called stable plaques, because these plaques tend not to separate from the blood vessel wall and are stable. On the other hand, the fatty and bleeding plaques are called unstable or movable plaques, because these plaques tend to separate from the blood vessel wall and tend to be unstable. Unstable plaque is given a movement by a pressure such as bloodstream, and, at a certain point, is separated from the blood vessel wall. When the plaque is separated from the blood vessel wall, a sequence of pathoses is caused, including formation of a thrombus, narrowing of the internal cavity of the blood vessel, and closure of the blood vessel, resulting in cerebral infarction and myocardial infarction.

In some cases, there is a portion in a part of the unstable plaque that sways according to a change of a bloodstream due to the heartbeat. For example, this portion moves up and down in a floating manner, or moves in a movement similar to an expansion and contraction movement of a jellyfish in response to the bloodstream. The former is called a floating plaque and the latter is called a jellyfish sign. In the following description, the swaying portion of the unstable plaque which is further unstable will be called a "free-moving piece". The free-moving piece is a part which may be separated from the blood vessel wall in the near future, which may be detached from the plaque body, and which may form a thrombus.

Diagnosis of the plaque by an ultrasonic diagnosis device has advantages; for example the property of the plaque can be classified by the brightness (intensity) of the echo, resolution is high, and the method is superior in real time diagnosis. JP 2009-148395 A discloses diagnosis of plaques using an ultrasonic tomographic image.

When the movement of the free-moving piece is to be observed in the ultrasonic tomographic image of the related art, recognizing the movement is difficult, because the movement is not so significant and is mixed in the movement of the blood vessel wall by the heartbeat.

An advantage of the present invention is that the free-moving piece is extracted and information on the position of the free-moving piece is provided.

SUMMARY

According to one aspect of the present invention, there is provided a processing device of an ultrasonic tomographic image, wherein positions of a reference image which is one image among a plurality of ultrasonic tomographic images which are sequentially obtained and which include a blood vessel wall on which an unstable plaque is attached and at least one of comparative images which are the images other than the reference image are matched by matching a position of a blood vessel wall surface, and a difference between the reference image and the comparative image is calculated in this state, to extract a free-moving piece.

In the calculation of the difference between the reference image and the comparative image, a binarization process is executed. In this case, because information on the unstable plaque portion; in particular, the portion in contact with the bloodstream section, is desired, a value between the brightness of the plaque and the brightness of the bloodstream section is used as the threshold value. In the difference image, a portion where values of the brightness (binary value) of the reference image and that of the comparative image differ from each other is extracted. Because there may be cases where a boundary surface between the blood vessel wall and the bloodstream (surface of blood vessel) or between the plaque and the bloodstream does not completely match in the position matching process, there can be employed a configuration where only a portion having a thickness in a direction intersecting the blood vessel wall is greater than or equal to a predetermined value is extracted.

The obtained difference image can be provided overlapping the reference image or the comparative image of multiple values. The difference image can be provided in a distinguishable form from the reference image or the like of the multiple values. For example, the reference image may be displayed with reduced brightness and the difference image may be displayed with high brightness. Alternatively, the difference image may be colored. By comparing the reference image and each of the comparative images to obtain difference images and sequentially displaying the difference images, it is possible to display a video image which allows viewing of the movement of the free-moving piece.

According to various aspects of the present invention, it is possible to clearly display the free-moving piece having a particularly high probability of separation among the unstable plaques attached to the blood vessel wall.

DESCRIPTION OF EMBODIMENT

Figure 1:
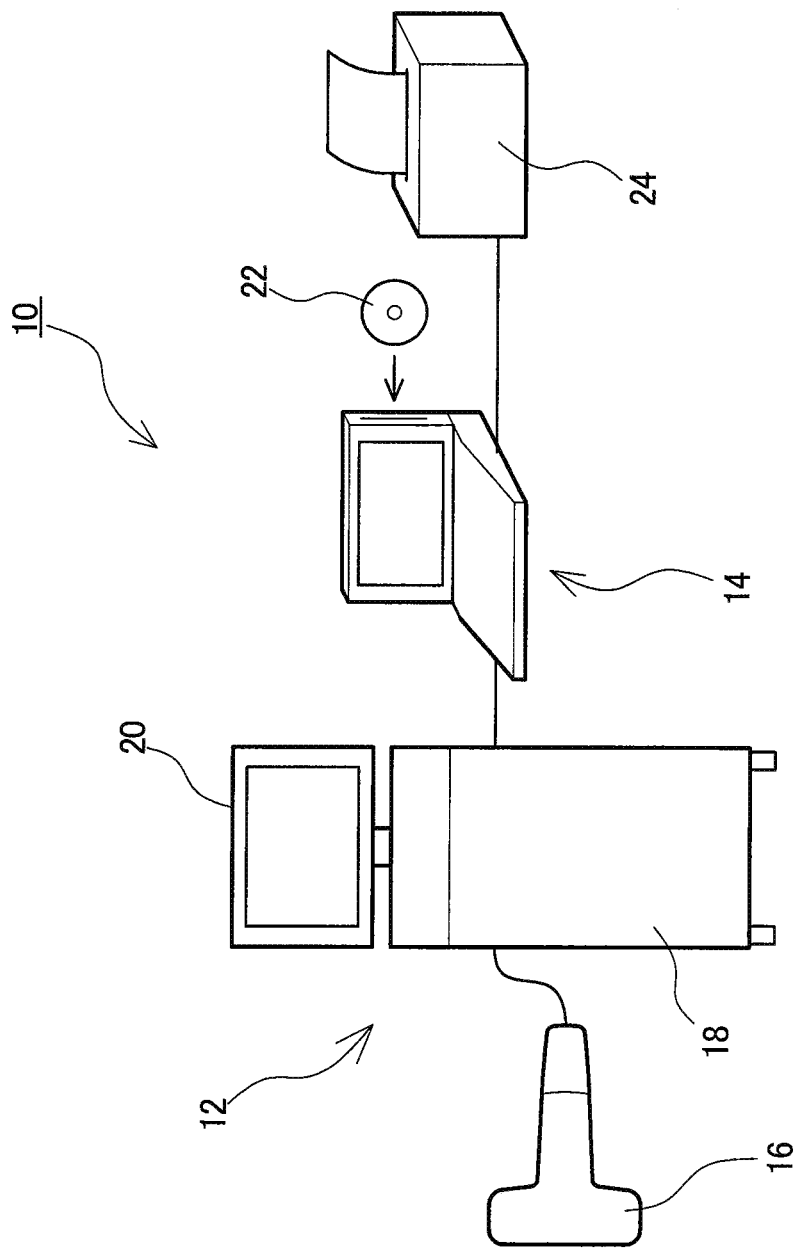
FIG. 1 is a schematic structural diagram of an ultrasonic diagnosis system according to a preferred embodiment of the present invention.

A preferred embodiment of the present invention will now be described with reference to the drawings. FIG. 1 is a diagram schematically showing a structure of an ultrasonic diagnosis system 10 according to a preferred embodiment of the present invention. The ultrasonic diagnosis system 10 comprises an ultrasonic diagnosis device 12 and a computer 14. The ultrasonic diagnosis device 12 comprises an ultrasonic probe 16 which transmits and receives ultrasound to and from a subject, a device body 18 having an image formation unit which forms a predetermined ultrasonic image such as a tomographic image based on the received reflected wave of the ultrasound, and a display 20 which displays the formed image. The computer 14 is connected to the ultrasonic diagnosis device 12, and can capture the ultrasonic image formed by the ultrasonic diagnosis device 12. The computer 14 can read a predetermined program from an external storage medium 22 such as a DVD. In addition, a printer 24 can be connected to the computer 14, and the ultrasonic image may be printed and output on paper as necessary.

The system 10 shown in FIG. 1 shows an example configuration of the system structure, and the system may alternatively be formed in other configurations. For example, the function of the computer 14 may be integrated in the ultrasonic diagnosis device 12.

Figure 2:
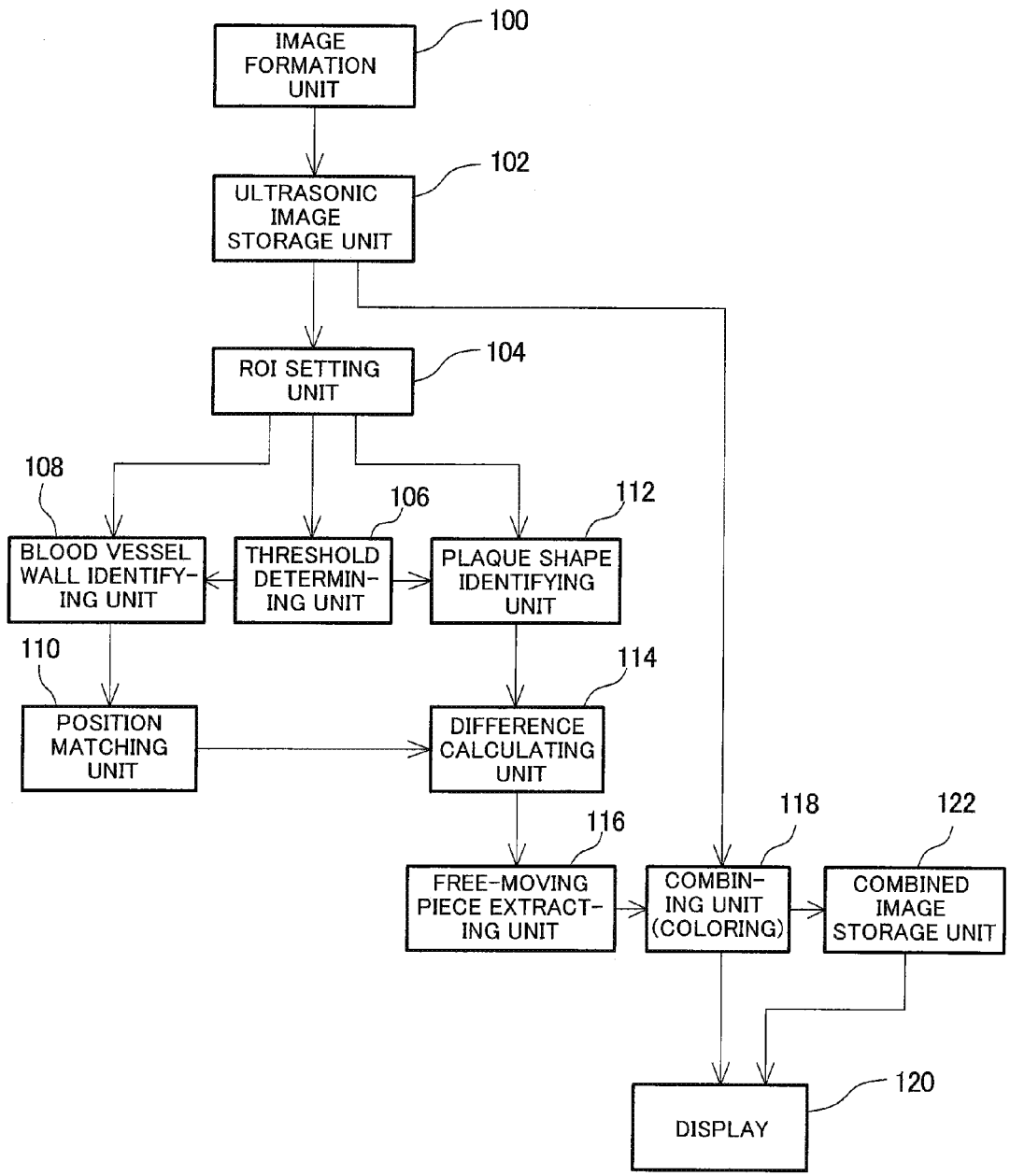
FIG. 2 is a block diagram showing a structure of an image process according to a preferred embodiment of the present invention.
Figure 3:
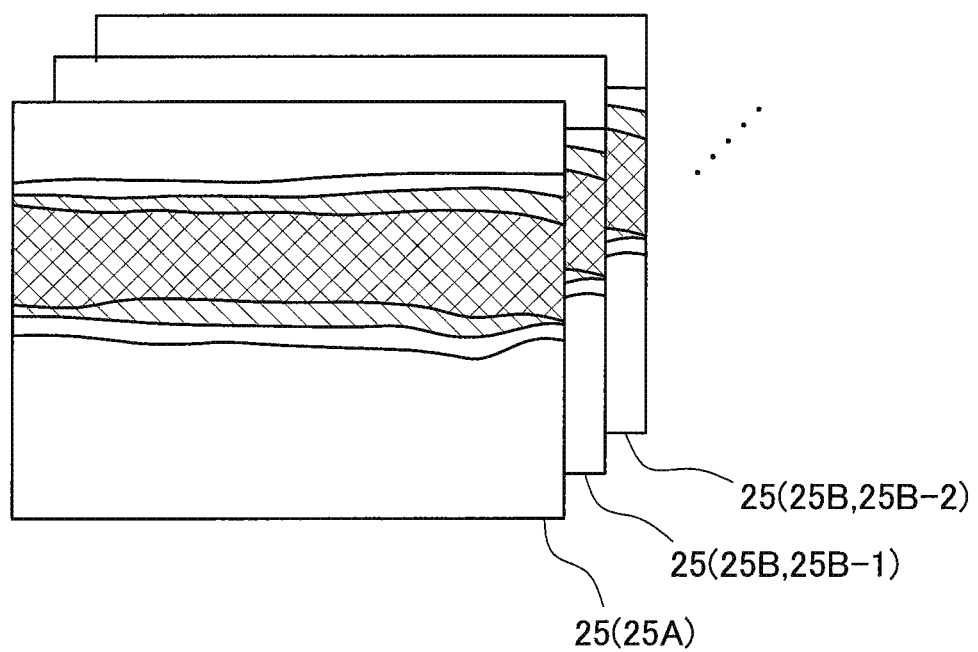
FIG. 3 is a diagram showing a plurality of ultrasonic tomographic images.

FIG. 2 is a block diagram showing a structure of an image process executed by the ultrasonic diagnosis system 10. An image formation unit 100 forms an ultrasonic tomographic image based on the reflected wave of the ultrasound. The formation of the ultrasonic tomographic image is identical to that in the image formation in the ultrasonic diagnosis device of the related art, and, thus, will not be described here. In the image formation unit 100, ultrasonic tomographic images are successively formed at a predetermined frame rate and the formed images 25 are sequentially stored in an ultrasonic image storage unit 102 (refer to FIG. 3). The image 25 to be stored may be all frames, or the number of frames may be thinned out. In order to observe the movement of the unstable plaques due to change in the bloodstream, it is preferable to obtain and store, for one heartbeat, a plurality of or more than a few images.

Figure 4:
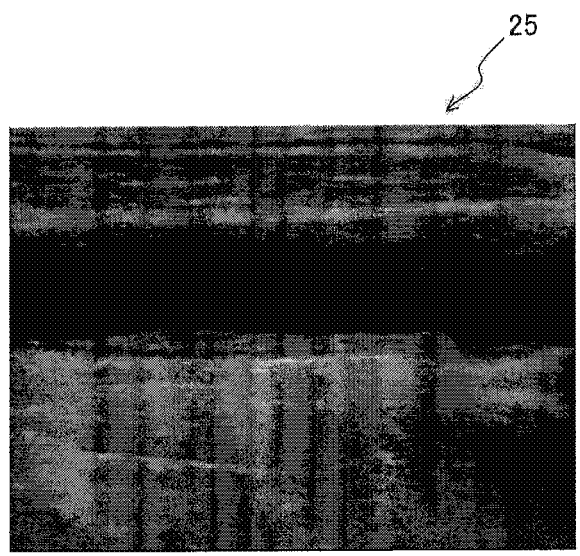
FIG. 4 is a diagram showing an example of an ultrasonic tomographic image (multiple values).
Figure 5:
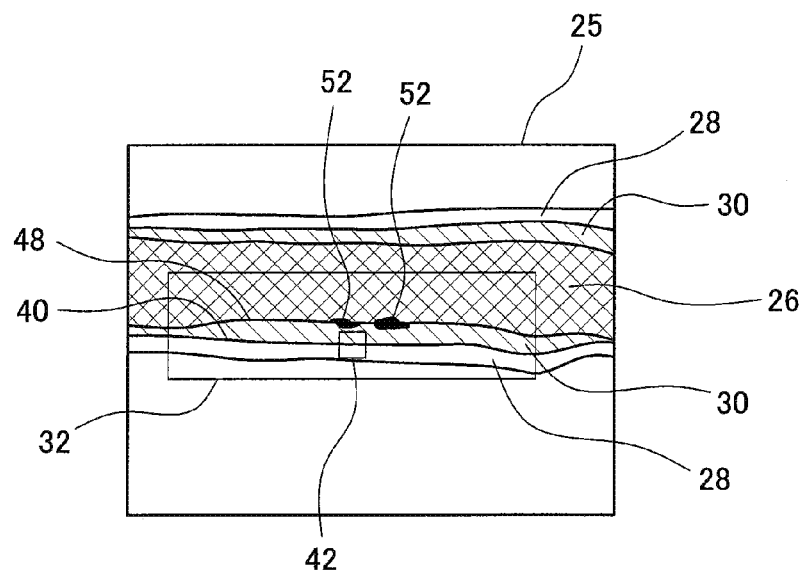
FIG. 5 is a diagram in which the ultrasonic tomographic image of FIG. 4 is simplified.

FIG. 4 shows an example of the obtained image. FIG. 5 is a diagram simplifying the grayscale image of FIG. 4 for the purpose of explanation. FIGS. 4 and 5 show images showing a cross section including an axis of the carotid artery. A portion in the blood vessel where the blood flows (bloodstream section) 26 is dark, and a blood vessel wall 28 and a muscle tissue are bright. An unstable plaque 30 formed on the inner wall surface of the blood vessel is a tissue which is softer than the blood vessel wall or the like, and has a brightness which is darker then the blood vessel wall, but brighter than the bloodstream section 26, which is liquid. In order to observe the movement of the unstable plaque due to the change of the bloodstream, it is preferable to obtain and store a plurality of or more than few images for one heartbeat.

Next, a region of interest (ROI) 32 is set (ROI setting unit 104). The region of interest 32 is determined by the user while viewing one or a plurality of the formed images. More specifically, for example, the ultrasonic image is displayed on the display of the computer 14, a rectangle indicating the region of interest 32 is displayed in an overlapped manner, and the rectangle is moved and expanded/contracted with an input device of the computer 14 such as a mouse and a keyboard, to set the region of interest 32. An image in which the region of interest 32 is set will hereinafter be referred to as a "reference image 25A", and the images other than the reference image will hereinafter be referred to as "comparative images 25B". Moreover, when it is necessary to distinguish between the plurality of comparative images for the purpose of explanation, the comparative images will be assigned branch numbers (−1, −2, . . . ) in the time sequential order, such as 25B-1, 25B-2, . . . . The reference image 25A is preferably a telesystolic or telediastolic image of the heart, and cardiograph information is preferably obtained for this purpose. The free-moving piece in the unstable plaque may be considered to be at a position most distant within the movement width at the telesystolic or telediastolic time. Therefore, the difference can be most clearly obtained by comparing the positions at the telesystolic or telediastolic and the positions of other times.

Figure 6:
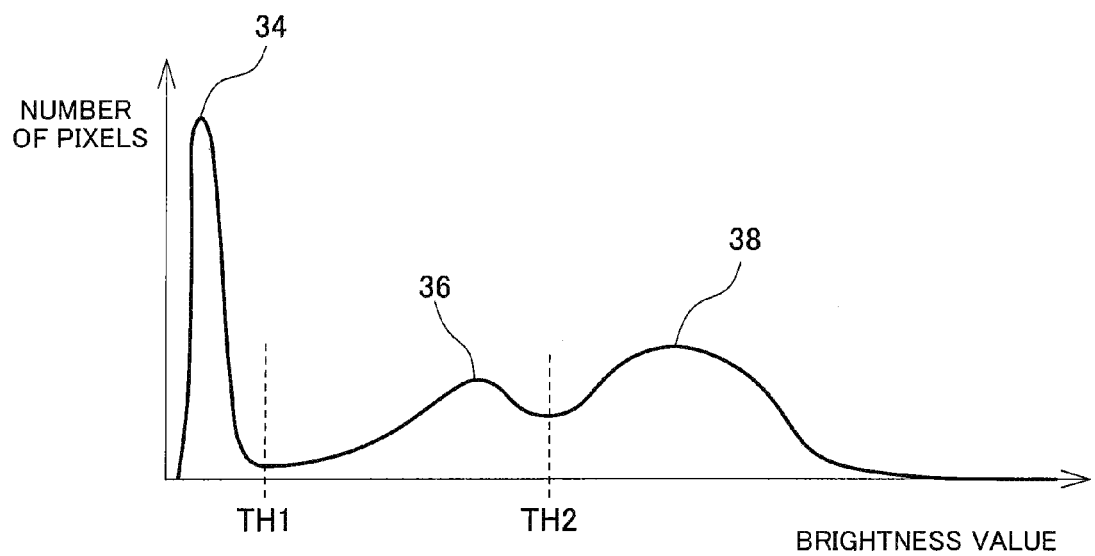
FIG. 6 is a diagram showing a relationship between a brightness value and a number of pixels.

Then, for pixels in the set region of interest 32, the appearance frequency (number of pixels) of each brightness value is plotted in a graph. FIG. 6 is a graph in which the brightness value is set on the horizontal axis and the number of pixels is set on the vertical axis. The graph shows the number of pixels of a certain brightness value in the region of interest 32. In FIG. 6, the number of pixels of certain brightness value is not shown without processing, but a certain processing is applied to smoothen the numbers and obtain a smooth curve. From the graph of occurrence frequency of FIG. 6, it can be seen that there are three peaks. A mountain including a first peak 34 having the brightness at the lowest position corresponds to the pixels of the bloodstream section 26. The region around a second peak 36 having the brightness at the next lowest position corresponds to the pixels of the unstable plaque 30. The region around a third peak 38 having the brightness at the highest position corresponds to the pixels of the blood vessel wall 28 or the like. By setting a threshold value at a position in the valleys between these peaks, in particular, the position of lowest frequency between the peaks, it is possible to distinguish the bloodstream section 26, blood vessel wall 28, and unstable plaque 30 on the ultrasonic tomographic image. In other words, with a first threshold value TH1 between the first peak 34 and the second peak 36, the pixels of unstable plaque 30 and the blood vessel wall 28 can be distinguished from the pixels of the bloodstream section 26. With a second threshold value TH2 between the second peak 36 and the third peak 38, the pixels of the bloodstream section 26 and the unstable plaque 30 can be distinguished from the pixels of the blood vessel wall 28. A threshold value setting unit 106 determines the first threshold value TH1 and the second threshold value TH2 based on the graph showing the relationship between the brightness value and the number of pixels having that brightness value. Alternatively, predetermined values maybe used for the threshold values TH1 and TH2 as a simplified method.

A blood vessel wall identifying unit 108 uses the second threshold value TH2 to apply a binarization process on the reference image 25A and the comparative images 25B. As described above, the second threshold value TH2 is a value for distinguishing the plaque 30 and the blood vessel wall 28. Therefore, a boundary of binarization image obtained as a result of this binarization process corresponds to an inner wall surface 40 (refer to FIG. 5) of the blood vessel wall. After the binarization process, a noise removal process may be applied. The noise removal process may be, for example, a process to remove isolated pixels using a labeling process. A window 92 is set on the boundaries in the binarization images for a position matching of the reference image 25A and the comparative images 25B, to be described later. The window 42 is set at a predetermined position in a left and right direction of the region of interest 32 represented by a rectangle, preferably a center position, and where the numbers of bright and dark pixels are approximately equal to each other. As the method of setting, for example, the window 42 of 5×5 is moved from the top to the bottom along a center line of the region of interest 32, and a position where the numbers of bright and dark pixels are closest to each other is set as the position of the window 42. As a result, the inner wall surface of the blood vessel 40 crosses the window 42 to approximately bisect the window 42.

Figure 7:
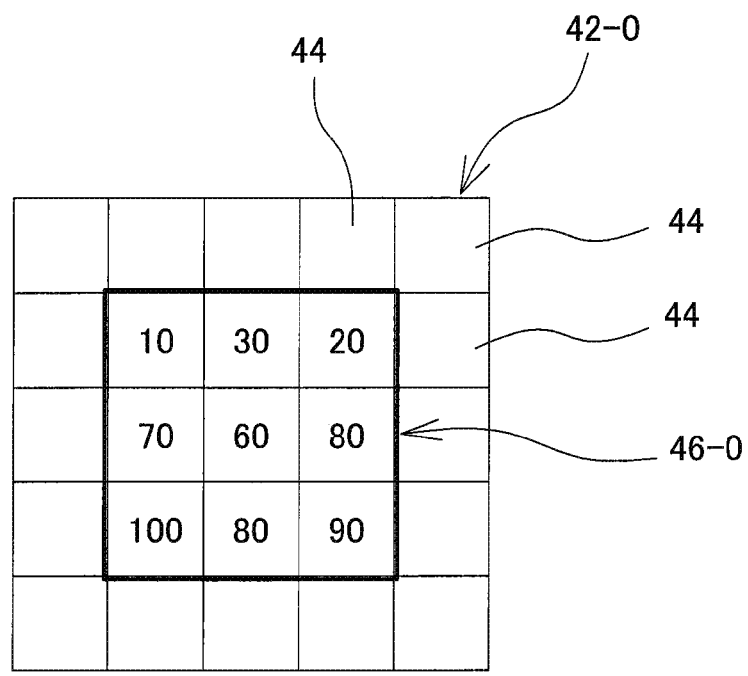
FIG. 7 is a diagram showing an example window which is set for a reference image.
Figure 8:
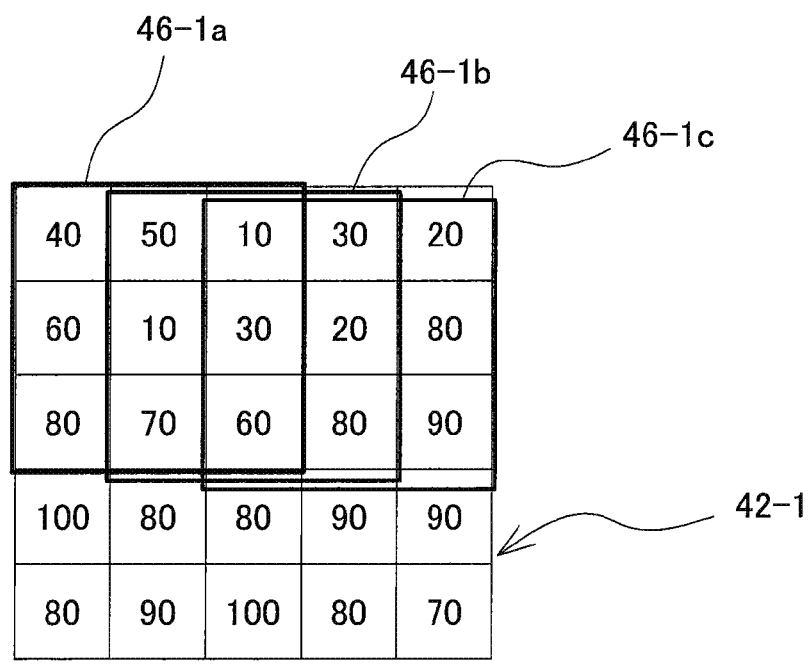
FIG. 8 is a diagram showing an example window which is set for a comparative image.

The position of the comparative image is matched with that of the reference image by a position matching unit 110 using the window 42. The window which is set for the reference image 25A is assigned reference numeral 42-0. As shown in FIG. 7, the window 42-0 comprises, for example, 5×5 pixels 44. At a position inside the window 42-0, a comparative region 46-0 which is smaller than the window 42-0 and which comprises, for example, 3×3 pixels is set at the center of the window 42-0. The window 92-0 and the comparative region 46-0 are set for the multiple-value image before the binarization process of the reference image, and brightness values of the pixels in the comparative region 46-0 are obtained. For the reference numeral of the comparative region also, the branch number (−0) is attached to indicate that the comparative region is a comparative region 46 related to the reference image 25A. In FIG. 7, the brightness values of the pixels are described for the pixels in the comparative region 46-0. In a comparative image (multiple value) 25B-1 which is obtained subsequent to the reference image 25A; that is, the comparative image obtained next to the reference image 25A among the images which are successively obtained, a window 42-1 is set at the same position as the reference image 25A, and brightness value information of 5×5 pixels of the window 42-1 is obtained. To the window 42 and the comparative region 46 which are set for the comparative image 25B-1, a branch number (−1) is attached. FIG. 8 shows brightness values of the pixels in the window 92-1 of the comparative image 25B-1. Comparative regions, of 3×3, 46-1a, 46-1b, 46-1c, . . . are sequentially set in the window 42-1, and, based on the correlation with the comparative region 46-0 of the reference image, a shift between the position of the inner wall surface of the blood vessel in the reference image and that in the comparative image is calculated.

More specifically, first, the comparative region 96-0 of the reference image and the comparative region 46-1a of the comparative image are compared. A sum Z of squares of differences in the brightness values of the pixels of comparative regions of row 1 and column 1, row 1 and column 2, row 1 and column 3, row 2 and column 1, . . . row 3 and column 3 is calculated.

$$Z = \sum_i \sum_j \{F(n)ij - F(n+1)ij\}^2 \qquad \text{[Equation 1]}$$

Here, F(n)ij represents a pixel value of an ith row and a jth column of the comparative region 46-0 of the reference image, and F(n+1)ij represents a pixel value of the ith row and the jth column of the comparative region 46-1a of the comparative image.

The comparative region is sequentially moved, a sum Z is calculated for each comparative region, and a comparative region 46-1 with the smallest sum Z is determined. In the illustrated example configuration, the comparative region 46-1c has the smallest sum Z. In other words, the image pattern having the highest correlation with the image pattern in the comparative region 46-0 of the reference image is the comparative region 46-1c. Based on this determination, the portion displayed in the comparative region 46-0 of the reference image can be considered to have moved in the comparative image to the comparative region 46-1c which is shifted to the right and upward by one pixel. Based on this, the position of the blood vessel wall in the comparative image is assumed to be shifted by one pixel to the right and upward from that of the reference image. By moving the entire comparative image by this shift, it is possible to overlap the position of the blood vessel wall of the comparative image with that of the reference image. The sizes of the window 42 and the comparative region 46 in the window may be different from those described above. For the other comparative images 25B-2, 25B-3, . . . also, the shift with respect to the reference image 25A is determined in a similar manner.

Because the free-moving piece of the unstable plaque can be thought to exist on the surface of the plaque, a plaque shape identifying unit 112 identifies a shape of the surface 48 of the unstable plaque (refer to FIG. 5). For this purpose, the first threshold value TH1 described above is used. As shown in FIG. 6, because the first threshold value TH1 is a value between the unstable plaque 30 and the bloodstream section 26 or between the blood vessel wall 28 and the bloodstream section 26, when the binarization process using the first threshold value TH1 is executed, the boundary between brightness and darkness would represent the surface 48 of the unstable plaque or the surface of the blood vessel wall.

Figure 9:
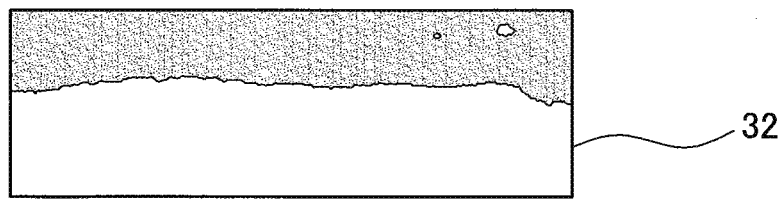
FIG. 9 is a diagram showing an ultrasonic tomographic image in which a surface of the unstable plaque is displayed by binarization.
Figure 10A:
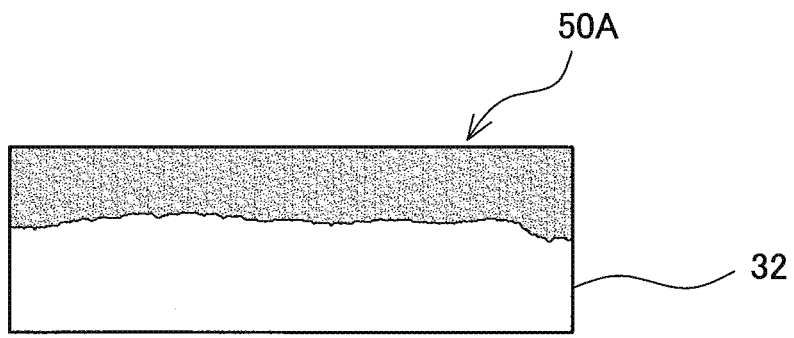
FIG. 10A is a diagram showing an ultrasonic tomographic image in which noise is removed from the image of FIG. 9.
Figure 10B:
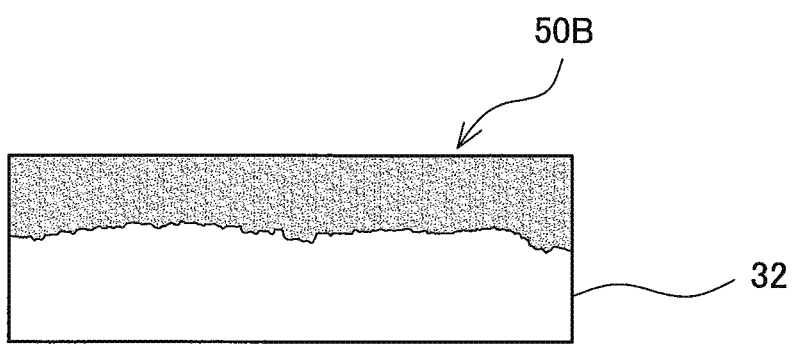
FIG. 10B is a diagram showing an ultrasonic tomographic image in which noise is removed in the comparative image.

FIG. 9 shows an image obtained by binarizing the pixels in the region of interest 32 using the first threshold value TH1. In FIG. 9, the gray area represents the dark portion. The shape of the surface 48 of the unstable plaque is clearly shown as a boundary between brightness and darkness. FIG. 9 also has noise in the bloodstream section, and a process for removing the noise may be applied. More specifically, a labeling process may be applied, and an isolated bright portion may be removed as noise. A result of the noise removal is shown in FIG. 10A. The binarization process using the first threshold value TH1 and the noise process are executed for the reference image 25A and the comparative image 25B-1; in particular, for the image in the region of interest. A result of binarization and noise process and noise process of the comparative image 25B-1 is shown in FIG. 10B. In FIGS. 10A and 10B also, similar to FIG. 9, the gray area represents the dark portion. The reference image and the comparative image binarized with the first threshold value TH1 will hereinafter be referred to as the referenced image 50A and the comparative image 50B (50B-1).

Figure 11:
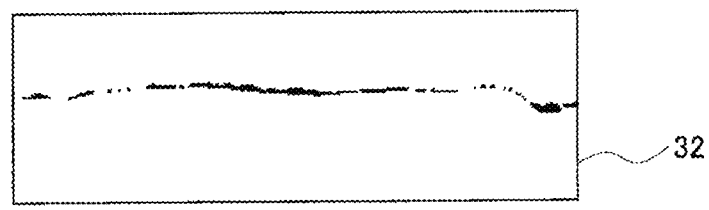
FIG. 11 is a diagram showing a difference image.

A difference calculating unit 114 calculates a difference in the region of interest between the binarized reference image 50A and the binarized comparative image 50B-1. In this process, the binarized comparative image 50B-1 is moved based on the shift between the reference image 25A and the comparative image 25B-1 calculated by the position matching unit 110, and then, the difference is calculated. In other words, the binarized comparative image 50B-1 is translated to resolve the shift and the difference is calculated in this state. With this process, the image patterns would approximately overlap each other between the binarized reference image 50A and the binarized comparative image 50B-1. When the brightness values of the binarized pixels are 0 (dark) and 1 (bright), the difference is one of −1, 0, and 1. If there is no moved portion between the binarized reference image 50A and the binarized comparative image 50B-1, the difference would be 0 for all pixels. The pixels having values of −1 or 1 represent portions of the binarized comparative image 50B-1 which have moved with respect to the binarized reference image 50A. In FIG. 11, the actual brightness and darkness are inverted, and the pixel having a difference of 0 is represented as bright and the pixel having a difference of −1 or 1 is represented as dark. In other words, the portion which has moved is represented as dark.

Figure 12:
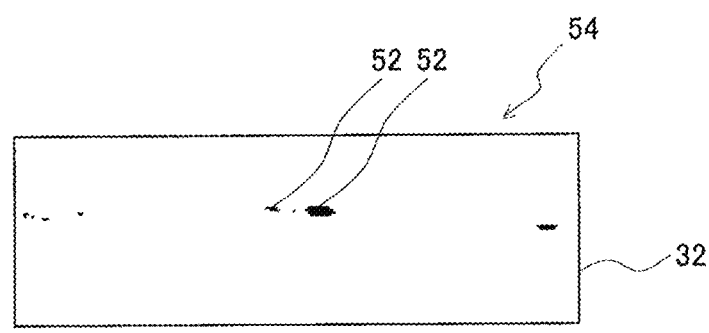
FIG. 12 is a diagram showing an ultrasonic tomographic image in which an unnecessary plaque boundary portion is removed and a free-moving piece is extracted from the image of FIG. 11.

Although the position matching unit 110 applies position matching for the reference image 25A and the comparative image 25B, in reality, there may be cases where a slight shift remains. This may be considered a primary reason for the area of the dark pixels being relatively wide in FIG. 11. After the position matching process, the amount of remaining shift should be small, and a free-moving piece extracting unit 116 considers a narrow portion having a width of less than or equal to a predetermined width in a direction intersecting the blood vessel wall in the dark pixel portion as an error in the position matching process, and removes this portion. The remaining portion is extracted as a free-moving piece 52 as shown in FIG. 12, and a difference image 54 (54-1) is obtained. In the present embodiment, the direction intersecting the blood vessel wall is in the up and down direction of the region of interest 32, a portion having a width of one pixel in this direction is removed, and a portion having a width of 2 or more pixels is extracted as the free-moving piece 52. The process to remove the pixel portion having a narrow width may be omitted when the result of the position matching is superior and the free-moving piece 52 can be extracted with sufficient clarity.

A combining unit 118 applies colors to the extracted free-moving piece 52 in the obtained difference image, so that the free-moving piece 52 can be displayed on the display 120 in an overlapping manner over the reference image or the comparative image. In addition, for the reference image 25A and the plurality of comparative images 25B-2, 25B-3, . . . , the difference images 54 (54-2, 54-3, . . . ) may be calculated in a similar manner and stored in a combined image storage unit 122, to allow a video image display by successively displaying the stored images. In the video image, while the reference image 25A of multiple values is displayed, the difference images 54-1, 54-2, 54-3, . . . may be sequentially displayed to show the movement of the free-moving piece. Alternatively, comparative images 25B-1, 25B-2, 25B-3, . . . of multiple values may be sequentially displayed and the difference images 54-1, 54-2, 54-3, . . . may be displayed in synchronization with and overlapping the display of the comparative images. In this case, the comparative images 25B-1, 25B-2, 25B-3, . . . are desirably displayed while being translated to compensate for the shift with respect to the reference image 25A determined by the position matching unit 110.

Each of the functional blocks of image process shown in FIG. 2 is realized by a calculating unit, a storage unit, etc. of a computer functioning according to a predetermined program. The program can be recorded on an external storage medium 22 in a manner to be readable by a computer.

In addition to being colored and overlapped with the reference image 25A, the difference image 54 may be overlapped in a manner such that the overall brightness of the reference image 25A is reduced and the brightness of the difference image 54 is set at the upper limit value or a value close to the upper limit value. In this case, the free-moving piece 52 is displayed brighter than the surroundings.

What is claimed is:

1. A processing device of an ultrasonic tomographic image, comprising:
  a position matching means for matching positions of a reference image and a comparative image by matching a position of a blood vessel wall surface in the reference image and the comparative image, wherein the reference image is one of a plurality of ultrasonic tomographic images which are successively obtained and which include a blood vessel wall on which an unstable plaque is attached, and the comparative image is an image other than the reference image;
  a binarization means for binarizing the reference image and the comparative image using a threshold value with which the unstable plaque and a bloodstream section are distinguished, so as to define a boundary between the unstable plaque and the bloodstream, the positions of the reference image and the comparative image having been matched by the position matching means;
  a difference image obtaining means for (i) calculating a difference between the binarized reference image and the binarized comparative image at the boundary between the unstable plaque and the bloodstream section, and (ii) obtaining a difference image showing a free-moving piece at a portion of the boundary between the unstable plaque and the bloodstream section where the difference between the binarized reference image and the binarized comparative image is greater than or equal to a predetermined value, the difference defining a shift in a position of a surface of the unstable plaque between the binarized reference image and the binarized comparative image, so as to distinguish a movement of the free-moving piece from a movement of the unstable plaque and the bloodstream section; and
  a difference image providing means for providing the difference image.

2. The processing device of ultrasonic tomographic image according to claim 1, wherein
  the difference image providing means provides the difference image overlapped over the reference image or the comparative image and in a distinguishable form from the reference image or the comparative image.

3. The processing device of ultrasonic tomographic image according to claim 2, wherein
  the distinguishable form is achieved by coloring the difference image.

4. The processing device of ultrasonic tomographic image according to claim 1, wherein
  the difference image obtaining means obtains a plurality of difference images by comparing a plurality of binarized comparative images to the binarized reference image, and
  the difference image providing means displays a video image of the plurality of difference images.

5. An ultrasonic diagnosis system comprising:
  an image obtaining means for successively obtaining ultrasonic tomographic images including a blood vessel wall on which an unstable plaque is attached;
  a position matching means for matching positions of a reference image and a comparative image by matching a position of a blood vessel wall surface in the reference image and the comparative image, wherein the reference image is one of a plurality of ultrasonic tomographic images which are successively obtained and which include a blood vessel wall on which an unstable plaque is attached, and the comparative image is an image other than the reference image;

a binarization means for binarizing the reference image and the comparative image using a threshold value with which the unstable plaque and a bloodstream section are distinguished, so as to define a boundary between the unstable plaque and the bloodstream, the positions of the reference image and the comparative image having been matched by the position matching means;

a difference image obtaining means for (i) calculating a difference between the binarized reference image and the binarized comparative image at the boundary between the unstable plaque and the bloodstream section, and (ii) obtaining a difference image showing a free-moving piece at a portion of the boundary between the unstable plaque and the bloodstream section where the difference between the binarized reference image and the binarized comparative image is greater than or equal to a predetermined value, the difference defining a shift in a position of a surface of the unstable plaque between the binarized reference image and the binarized comparative image, so as to distinguish a movement of the free-moving piece from a movement of the unstable plaque and the bloodstream section; and a difference image providing means for providing the difference image overlapped over the reference image or the comparative image and in a distinguishable form from the reference image or the comparative image.

6. The ultrasonic diagnosis system according to claim 5, wherein
the difference image providing means provides the difference image overlapped over the reference image or the comparative image and in a distinguishable form from the reference image or the comparative image.

7. The ultrasonic diagnosis system according to claim 6, wherein
the distinguishable form is achieved by coloring the difference image.

8. The ultrasonic diagnosis system according to claim 5, wherein
the difference image obtaining means obtains a plurality of difference images by comparing a plurality of binarized comparative images to the binarized reference image, and
the difference image providing means displays a video image of the plurality of difference images.

9. The processing device of an ultrasonic tomographic image according to claim 1, wherein the reference image is an ultrasonic tomographic image obtained at a telesystolic time or a telediastolic time.

10. The ultrasonic diagnosis system according to claim 5, wherein the reference image is an ultrasonic tomographic image obtained at a telesystolic time or a telediastolic time.

* * * * *